United States Patent
Nagai et al.

(10) Patent No.: US 6,615,662 B2
(45) Date of Patent: Sep. 9, 2003

(54) THREE-DIMENSIONAL ULTRASONIC SCAN PROBE

(75) Inventors: Hiroshi Nagai, Tokyo (JP); Norio Tomita, Tokyo (JP); Kohei Ono, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 09/839,352

(22) Filed: Apr. 20, 2001

(65) Prior Publication Data
US 2001/0032511 A1 Oct. 25, 2001

(30) Foreign Application Priority Data
Apr. 20, 2000 (JP) ........................................ 2000-119201

(51) Int. Cl.[7] ............................. G01N 29/04; A61B 8/00
(52) U.S. Cl. ............................. 73/618; 73/606; 73/607; 73/628; 600/443
(58) Field of Search ........................ 73/618, 628, 642, 73/644, 606, 607; 600/443, 459, 467

(56) References Cited

U.S. PATENT DOCUMENTS

| | | | | |
|---|---|---|---|---|
| 4,570,488 A | | 2/1986 | Miwa et al. ................... 73/626 |
| 4,580,451 A | | 4/1986 | Miwa et al. ................... 73/626 |
| 5,050,137 A | * | 9/1991 | Sato et al. ..................... 367/150 |
| 5,211,059 A | * | 5/1993 | Hayakawa et al. ............ 73/606 |
| 5,524,354 A | * | 6/1996 | Bartzke et al. ................. 33/558 |
| 5,797,845 A | * | 8/1998 | Barabash et al. ............. 600/443 |
| 5,999,840 A | * | 12/1999 | Grimson et al. .............. 600/424 |
| 6,059,728 A | * | 5/2000 | Ritter ............................ 600/443 |
| 6,102,860 A | * | 8/2000 | Mooney ........................ 600/443 |
| 6,122,967 A | * | 9/2000 | Sword ............................ 73/621 |
| 6,129,670 A | * | 10/2000 | Burdette et al. .............. 600/427 |
| 6,256,529 B1 | * | 7/2001 | Holupka et al. .............. 600/427 |
| 6,263,093 B1 | * | 7/2001 | Mochizuki .................... 382/128 |
| 6,511,433 B1 | * | 1/2003 | Benjamin ...................... 600/463 |

FOREIGN PATENT DOCUMENTS

| | | |
|---|---|---|
| JP | 58-185840 | 11/1982 |
| JP | 58-163348 | 9/1983 |

* cited by examiner

Primary Examiner—Hezron Williams
Assistant Examiner—Jacques Saint-Surin
(74) Attorney, Agent, or Firm—Hoffmann & Baron, LLP

(57) ABSTRACT

A plurality of ultrasonic transducer elements are arranged on the top surface of a probe, which is a concave spherical surface, so that ultrasonic beams transmitted from the ultrasonic transducer elements will intersect at a point coincident with the center of curvature of a curve delineated by the top surface. At this time, the acoustic lines conically propagate over a region beyond the point of intersection. Namely, the ultrasonic beams transmitted from the ultrasonic transducer elements pass through the point of intersection coincident with the center of curvature, and then conically and three-dimensionally propagate over the region beyond the point of intersection. Thus, acoustic lines are three-dimensionally transmitted to a wide region beyond an intercostal part of a physiological body or any other narrow space, and echoes returned from the region are received. Consequently, the wide region can be three-dimensionally monitored.

7 Claims, 3 Drawing Sheets

THREE-DIMENSIONAL ULTRASONIC SCAN PROBE

BACKGROUND OF THE INVENTION

1. Field of the Invention

The present invention relates to a three-dimensional ultrasonic scan probe including a plurality of ultrasonic transducer elements that transmit ultrasonic beams and receive echoes so as to enable real-time three-dimensional monitoring of a region to be measured.

2. Description of the Related Art

Japanese Unexamined Patent Publication No. 57-185840 has disclosed an ultrasonic diagnostic equipment in which ultrasonic transducer elements are arranged two-dimensionally in the form of a matrix in order to observe an organ or the like entirely. Any of the ultrasonic transducer elements is selected one after another and driven to transmit an ultrasonic beam with which an organ is electronically scanned. Echoes returned from the organ are synchronized and synthesized with one another. Consequently, a tomographic layer of the organ can be monitored.

However, when the equipment is used to monitor the entire heart, although a three-dimensional image can be produced based on echoes of ultrasonic beams that are transmitted from the numerous ultrasonic transducer elements and that pass an intercostal part, signal processing is complex. Moreover, since the ultrasonic transducer elements must be arranged mutually closely, the equipment becomes large in size. The equipment may be suitable for gynecologic examination rather than cardiology examination.

On the other hand, Japanese Unexamined Patent Publication No. 58-163348 (U.S. Pat. Nos. 4,570,488 and 4,580, 451) has disclosed an ultrasonic sector scan probe including an acousticlens. For enabling observation of the entire heart through an intercostal parts, a plurality of ultrasonic transducer elements are arranged so that ultrasonic beams transmitted from the ultrasonic transducer elements will intersect at a point to scan the heart in the form of a sector. An acoustic line is a locus of an ultrasonic beam. At this time, the acoustic lines are focused near the point of intersection at a measurable depth. The plurality of transducer elements are grouped in order to focusultrasonic beams in the form of a beam, and selected successively. Consequently, the heart is electronically scanned in the form of a sector. However, since an equipment including the probe is designed in order to monitor a two-dimensional tomographic layer, the equipment cannot produce a three-dimensional image of the heart by electronically scanning the heart with ultrasonic beams transmitted through an intercostal part.

SUMMARY OF THE INVENTION

Accordingly, an object of the present invention is to provide a three-dimensional ultrasonic scan probe for electronically scanning a region to be measured through a narrow part so as to enable three-dimensional observation of the object.

According to the present invention, there is provided a three-dimensional ultrasonic scan probe including a plurality of ultrasonic transducer elements that transmit ultrasonic beams and receive echoes so as to enable three-dimensional observation of a region to be measured. The plurality of ultrasonic transducer elements are arranged on the top surface of the probe, which is a concave spherical surface, so that ultrasonic beams transmitted from the ultrasonic transducer elements will intersect at a point coinciden twith the center of curvature of the top surface, and then conically propagate over the region to be measured located beyond the point of intersection.

Ultrasonic beams transmitted from the ultrasonic transducer elements intersect at a point coincident with the center of curvature of the top surface of the probe. After passing through the point of intersection, the acoustic lines three-dimensionally and conically propagate over the region to be measured located beyond the point of intersection. Namely, the ultrasonic beams are transmitted to a wide region located beyond the point of intersection that occupies an intercostal part or any other limited part of a human body, and echoes returned from the wide region are then received. In other words, the plurality of acoustic lines are irradiated three-dimensionally after passing through the common point of intersection. Consequently, the wide region is monitored three-dimensionally through the narrow space or any other narrow limited part.

Moreover, an acoustic lens may be placed on the top surface of the probe. A plurality of ultrasonic transducer elements may be arranged on the incidence surface of the acousticlens so that ultrasonic beams transmitted from the ultrasonic transducer elements will intersect at a point coincident with the focus of the acoustic lens, and conically propagate over a region beyond the point of intersection. In this case, the acoustic lines are three-dimensionally and conically irradiated to the region beyond the point of intersection coincident with the focus of the acoustic lens. Consequently, the entire heart or the left ventricle of the heart is monitored through an intercostal part.

In particular, for three-dimensionally monitoring the heart through an intercostal part, the three-dimensional ultrasonic scan probe is placed on the chest so that a point at which ultrasonic beams intersect will be located in the intercostal part. In this state, a maximum angle of diffusion at which the transmitted ultrasonic beams diffuse after passing through the point of intersection is preferably set to an angle permitting the ultrasonic beams to cover the entire heart or a portion of the heart that should be diagnosed. Consequently, despite the simple structure, the probe makes it possible to diagnose in real time a change in the volume of the entire heart or a portion of the heart through an intercostal part.

For enabling electronic scan using a larger number of acoustic lines than the limited number of ultrasonic transducer elements arranged near a narrow space, an electronic scanning means is used in combination with the plurality of ultrasonic transducer elements. The electronic scanning means successively selects a plurality of combinations of adjoining ultrasonic transducer elements, and drives each combination of ultrasonic transducer elements to transmit ultrasonic beams simultaneously. Owing to the electronic scanning means, a larger number of acoustic lines than the number of ultrasonic transducer elements can be transmitted to scan a region. This leads to improved accuracy in measurement, intensified ultrasonic power that is higher than the ultrasonic power offered by each ultrasonic transducer element,and an extended detection range.

The maximum angle of diffusion at which the ultrasonic beams transmitted from such plurality of ultrasonic transducer elements diffuse after passing through the point at which the ultrasonic beams intersect can be also set to an angle, which permits the ultrasonic beams to cover the entire heart, with said three-dimensional ultrasonic scan probe placed on the chest so that the point of intersection will be located in an intercostal part. This maximum angle of diffusion at which the ultrasonic beams diffuse is preferably set to approximately 60°.

BRIEF DESCRIPTION OF THE DRAWINGS

FIG. 4A is a sectional view of a probe having a concave lens, and FIG. 4B is a sectional view of a probe having a convex lens.

DESCRIPTION OF THE PREFERRED EMBODIMENTS

Figure 1:
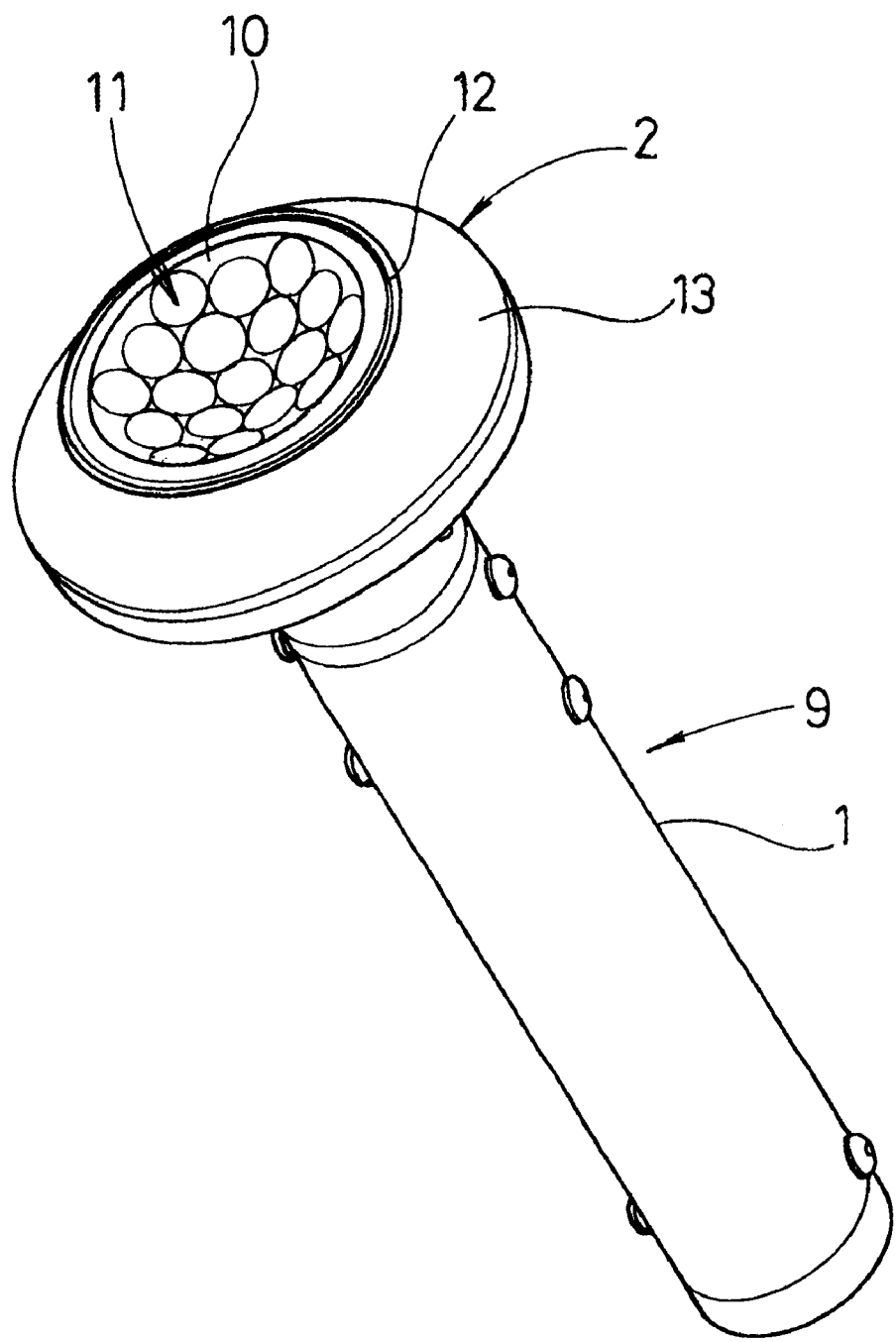
FIG. 1 is a perspective view of a three-dimensional ultrasonic probe in accordance with an embodiment of the present invention.

A three-dimensional ultrasonic scan probe for diagnosis of heart in accordance with an embodiment of the present invention will be described in conjunction with FIG. 1 to FIG. 3. As shown in FIG. 1, a head 2 is formed at the top end of a cylindrical hand-held member 1 of a probe 9. The head 2 has a top surface 10 that is a concave spherical surface on which nineteen ultrasonic transducer elements 11 are arranged. An annular edge 12 is formed on the perimeter of the top surface 10 for transthoracic monitoring. An inclined peripheral surface 13 is formed on the perimeter of the annular edge 12 so that it will withdraw laterally and gradually.

Figure 2:
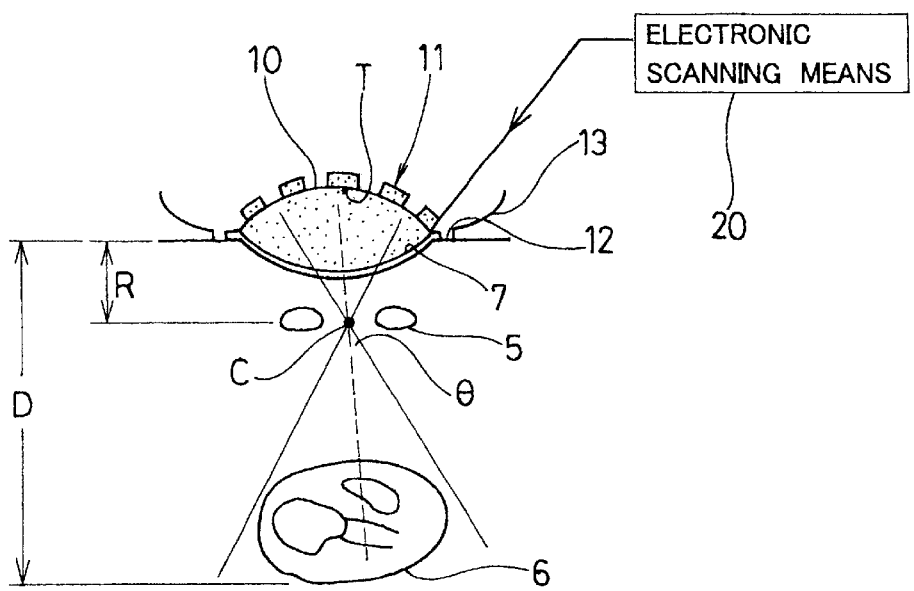
FIG. 2 is an explanatory diagram concerning actions performed by the probe.

As shown in FIG. 2, the top surface 10 that is a concave spherical surface is shaped so that when the annular edge 12 is in contact with the chest, the center of curvature of a curve delineated by the top surface 10 will be located in an intercostal part between ribs 5 on an extension of a segment linking the center T of the curve and the center point of the annular edge 12. Specifically, a standard range R from the annular edge 12 to the intercostal part is approximately 3 cm, and the radius of curvature of the curve delineated by the top surface 10 is set to approximately 4 cm. Consequently, ultrasonic beams transmitted from the ultrasonic transducer elements 11 arranged on the top surface 10 intersect at a point C coincident with the center of curvature and propagate over a region conically as if the acoustic lines delineated an umbrella.

Figure 3:
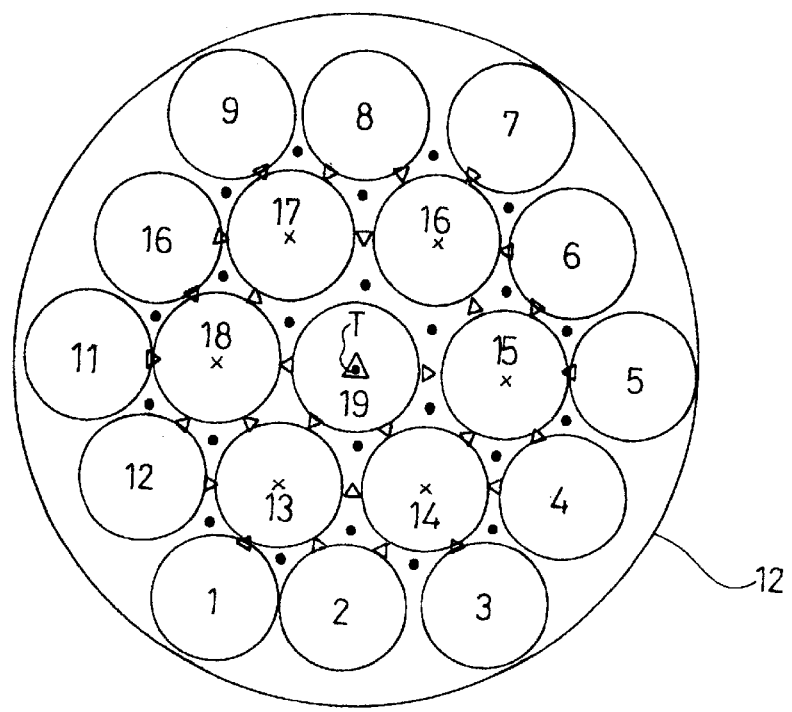
FIG. 3 is an explanatory diagram concerning the arrangement of ultrasonic transducer elements included in the probe.

The ultrasonic transducer elements 11 are, as virtually shown on a planar basis in FIG. 3, arranged so that five ultrasonic transducer elements will be juxtaposed along a diameter passing through the center T. Four ultrasonic transducer elements are juxtaposed across the five ultrasonic transducer elements on the diameter, and three ultrasonic transducer elements are juxtaposed outside the four ultrasonic transducer elements. Twelve ultrasonic transducer elements 11 are located along the perimete of the top surface, and driven to transmit ultrasonic beams simultaneously in units of three adjoining ones. An angle θ at which the synthesized acoustic lines conically propagate after passing through the point of intersection C is set to approximately 60°. Or in other words, a maximum angle of diffusion at which the acoustic lines diffuse after passing through the point of intersection C is set to approximately 60° so that the acoustic lines will cover the entire heart.

The three-dimensional ultrasonic scan probe 9 is, as shown in FIG. 2, used in combination with an electronic scanning means 20 so that the probe can be included in diagnostic equipment designed for diagnosing a change in the volume of the entire heart 6. The electronic scanning means 20 enables transmission of ultrasonic beams for scanning and reception of echoes. The electronic scanning means successively selects sixty-one combinations of three, four, and seven adjoining ultrasonic transducer elements 11 and allows the combinations to transmit ultrasonic beams simultaneously. This is intended to expand the area of an aperture offered by the probe 9 and increase the number of acoustic lines with which a region is scanned. An electronic scanning time required to achieve one scan composed of sixty-one steps is set to one-thirtieth sec on the assumption that the standard systole of the heart 6 is 200 msec. This signifies that seven scans are performed during the systole. The combinations of ultrasonic transducer elements will be described with the ultrasonic transducer elements 11 numbered as the first to nineteenth ultrasonic transducer elements as shown in FIG. 3.

As for combinations of three ultrasonic transducer elements, twenty-four combinations are created in total. Specifically, twelve combinations are created with the first, second, and thirteenth ultrasonic transducer elements, the second, third, and fourteenth ultrasonic transducer elements, etc., and the twelfth, first, and thirteenth ultrasonic transducer elements. Six combinations are created with the thirteenth, fourteenth, and second ultrasonic transducer elements, the fourteenth, fifteenth, and fourth ultrasonic transducer elements, etc., and the eighteenth, thirteenth, and twelfth ultrasonic transducer elements. Another six combinations are created with the thirteenth, fourteenth, and nineteenth ultrasonic transducer elements, the fourteenth, fifteenth, and nineteenth ultrasonic transducer elements, etc., and the eighteenth, thirteenth, and nineteenth ultrasonic transducer elements.

As for combinations of four ultrasonic transducer elements, thirty combinations are created in total. Specifically, six combinations are created with the first, second, thirteenth, and fourteenth ultrasonic transducer elements, the third, fourth, fourteenth, and fifteenth ultrasonic transducer elements, etc., and the eleventh, twelfth, thirteenth, and eighteenth ultrasonic transducer elements. Another six combinations are created with the first, second, twelfth and thirteenth ultrasonic transducer elements, the second, third, fourth and fourteenth ultrasonic transducer elements, etc., and the tenth, eleventh, twelfth, and eighteenth ultrasonic transducer elements. Another six combinations are created with the second, third, thirteenth, and fourteenth ultrasonic transducer elements, the fourth, fifth, fourteenth, and fifteenth ultrasonic transducer elements, etc., and the first, twelfth, thirteenth, and eighteenth ultrasonic transducer elements. Another six combinations are created with the second, thirteenth, fourteenth, and nineteenth ultrasonic transducer elements, the fourth, fourteenth, fifteenth, and nineteenth ultrasonic transducer elements, etc., and the twelfth, thirteenth, eighteenth, and nineteenth ultrasonic transducer elements. The other six combinations are created with the thirteenth, fourteenth, fifteenth, and nineteenth ultrasonic transducer elements, the fourteenth, fifteenth, sixteenth, and nineteenth ultrasonic transducer elements, etc., and the thirteenth, fourteenth, eighteenth, and nineteenth ultrasonic transducer elements.

As for combinations of seven ultrasonic transducer elements, seven combinations are created in total. Specifically, six combinations are created with the thirteenth, first, second, fourteenth, nineteenth, eighteenth, and twelfth ultrasonic transducer elements, the fourteenth, third, fourth, fifteenth, nineteenth, thirteenth, and second ultrasonic transducer elements, etc., and the eighteenth, tenth, eleventh, twelfth, thirteenth, nineteenth, and seventeenth ultrasonic transducer elements. One combination consists of the nineteenth, thirteenth, fourteenth, fifteenth, sixteenth, seventeenth, and eighteenth ultrasonic transducer elements.

When the thus structured three-dimensional ultrasonic scan probe 9 is used to monitor a change in the volume of the heart 6, ultrasonic beams are transmitted as described below. An acoustic propagation material 7 is applied to the concave part of the top surface 10. The hand-held member 1 is hold and the head is placed on the surface of a physiological body opposed to an intercostal part between ribs 5. Transmitting ultrasonic beams is then started. The electronic scanning means 20 successively selects the twenty-four combinations of three ultrasonic transducer elements and allows each combination of ultrasonic transducer elements to transmit ultrasonic beams simultaneously. The center of the synthesized ultrasonic beams transmitted from the three ultrasonic transducer elements of each combination is indicated with a dot mark •. Thereafter, the thirty combinations of four ultrasonic transducer elements are successively selected and driven to transmit ultrasonic beams simultaneously. The center of the synthesized ultrasonic beams transmitted from four ultrasonic transducer elements of each combination is indicated with a triangular mark Δ. Thereafter, the seven combinations of seven ultrasonic transducer elements are successively selected and driven to transmit ultrasonic beams simultaneously. The center of the synthesized ultrasonic beams transmitted from seven ultrasonic transducer elements of each combination is indicated with a cross mark X.

The ultrasonic beams transmitted from each combination of ultrasonic transducer elements are synthesized in a region to be measured after passing through the point of intersection C at which the acoustic lines intersect. Echoes of the synthesized ultrasonic beams are received synchronously with transmission. Consequently, the entire heart 6 is visualized with precision equivalent to sixty-one acoustic lines. Since the heart 6 is electronically scanned in cycles each of which is shorter than the systole of the heart 6, a change in the volume of the heart 6 can be monitored based on echoes returned from a plurality of concentric layers of the heart.

For further improving acoustic efficiency, acoustic lenses whose focal lengths are determined in order to focus acoustic lines within a typical diagnostic region may be placed on the faces of the nineteen transducer elements 11.

The electronic scanning means 20 may be designed to be able to switch modes. In this case, part of all the combinations may be used to electronically scan a portion of the heart as indicated with a dashed line in FIG. 2. Consequently, the portion of the heart obliquely including the left ventricle is scanned with acoustic lines that intersect at the point C and then propagate at an angle of approximately 30°. The heart may thus be diagnosed.

If a decrease in precision in measurement can be accepted to some extent, the first to nineteenth ultrasonic transducer elements 11 of the three-dimensional ultrasonic scan probe 9 may be successively driven to transmit an ultrasonic beam, though the ultrasonic powers of the transducer elements must be intensified. Thus, nineteen acoustic lines alone may be transmitted in order to monitor the entire heart by receiving echoes from a plurality of concentric layers of the heart. In this case, the ultrasonic beams transmitted from the first to twelfth ultrasonic transducer elements intersect at the point C and diffuse at an angle larger than 60°, because the ultrasonic beams are transmitted mutually independently. Consequently, the acoustic lines are conically irradiated to the heart. Moreover, the ultrasonic beams transmitted from the thirteenth to eighteenth ultrasonic transducer elements intersect at a point on a line passing through the center of the nineteenth ultrasonic transducer element 11, and diffuse at an angle smaller than 60°.

Figure 4A:
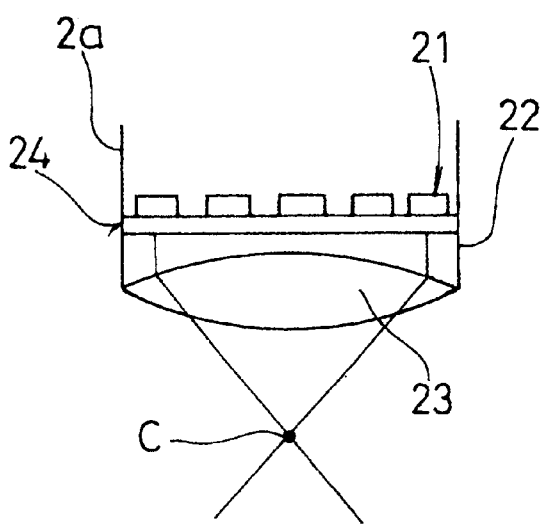
FIG. 4A and FIG. 4B show three-dimensional ultrasonic scan probes having acoustic lenses.
Figure 4B:
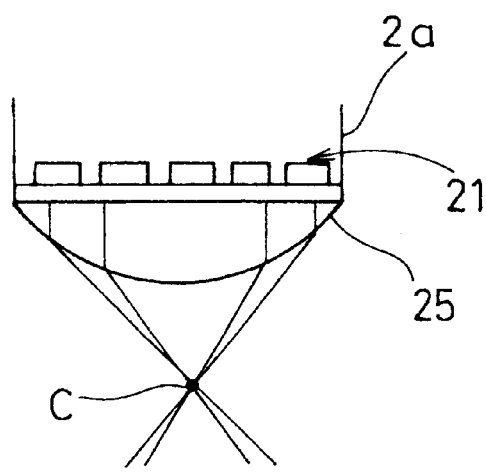

FIG. 4A and FIG. 4B show another embodiments each having an acoustic lens, on which ultrasonic transducer elements 21 are arranged, located at the top end of a head 2a. The embodiment shown in FIG. 4A employs a concave acoustic lens 22 that passes acoustic lines at a higher acoustic velocity than a living body does and which is made of, for example, acrylic. Nineteen ultrasonic transducer elements 21 are arranged on the round flat incidence surface of the acoustic lens 22 with a matching layer 24 between them, whereby a planar view of the heart can be provided. A solid acoustic propagation material 23 is placed on the concave part of the acoustic lens 22. The focal length of the acoustic lens 22 is determined so that the focus thereof coincident with a point C at which acoustic lines intersect will be located in an intercostal part between ribs 5 of a human body. At this time, the acoustic lines are conically irradiated to a region beyond the point of intersection C at an angle of approximately 60°. The effective aperture of the acoustic lens 22 is determined based on the distance to the rib 5 or the skin on the assumption that acoustic lines diffuse at the angle of approximately 60°. A paste-type acoustic medium may be applied to the concave part of the acoustic lens 22 every time measurement is performed. The ultrasonic transducer elements 21 may be independently and successively driven to transmit an ultrasonic beam. For intensifying ultrasonic power and increasing the number of scan steps, the ultrasonic transducer elements 21 may be combined as mentioned previously and driven to transmit ultrasonic beams simultaneously. In this case, the ultrasonic transducer elements need not be arranged spherically. Nevertheless, the same operation as the operation exerted when the ultrasonic transducer elements are arranged on a concave surface can be exerted.

FIG. 4B shows another embodiment that employs a convex acoustic lens 25 which passes acoustic lines at a lower acoustic velocity than a living body does and which is made by, for example, silicone. The ultrasonic transducer elements 21 are arranged on the round flat incidence surface of the acoustic lens 25. Moreover, the acoustic lens may be a Fresnel lens that has ultrasonic transducer elements arranged in the center of the flat incidence surface thereof and along a plurality of concentric circles on the flat incidence surface thereof. The flat incidence surface is made of synthetic resin. In this case, the Fresnel lens is shaped to have concave or convex parts thereof matched with the acoustic properties of ultrasonic transducer elements arranged concentrically or mutually individually.

Figure 5A:
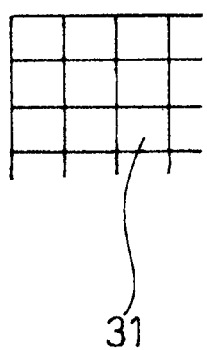
FIG. 5A, FIG. 5B, and FIG. 5C show arrangements of ultrasonic transducer elements adopted in another embodiments.
Figure 5B:
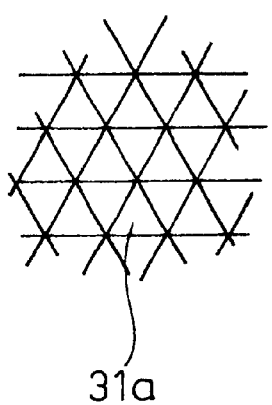
Figure 5C:
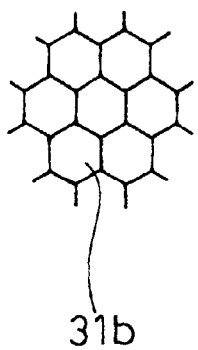

The present invention can be applied not only to medical uses including cardiology diagnosis but also to the purpose of three-dimensionally monitoring a region to be measured, which has a large volume and is located beyond a narrow space, by electronically scanning the region to be measured. FIG. 5A to FIG. 5C show another arrangements of ultrasonic transducer elements on the top surface of a probe that is a concave spherical surface or the incidence surface of an acoustic lens. Referring to FIG. 5A, ultrasonic transducer elements 31 are arranged in a grid array, in FIG. 5B, ultrasonic transducer elements 31a are in a triangular array, in FIG. 5C, ultrasonic transducer elements 31b are in a hexagonal honeycomb array. The number of ultrasonic transducer elements is not limited to nineteen, but can be varied according to a purpose of use, depending on the size of an irradiated region, the power spectrum of synthesized acoustic lines, or the precision in diagnosis.

What is claimed is:

1. A three-dimensional ultrasonic scan probe including a plurality of ultrasonic transducer elements that transmit ultrasonic beams and receive echoes so as to enable three-dimensional monitoring of a region to be measured, wherein:

said plurality of ultrasonic transducer elements are arranged on the top surface of said probe, which is a concave spherical surface, so that ultrasonic beams transmitted from said ultrasonic transducer elements will intersect at a point coincident with the center of curvature of a curve delineated by the top surface, and conically propagate over the region to be measured beyond the point of intersection.

2. A three-dimensional ultrasonic scan probe according to claim 1, wherein: the region to be measured is the heart; when said three-dimensional ultrasonic scan probe is placed on the chest so that the point at which ultrasonic beams transmitted from said ultrasonic transducer elements intersect will be located in an intercostal part of a physiological body, a maximum angle of diffusion at which the ultrasonic beams diffuse after passing through the point of intersection is set to an angle permitting the ultrasonic beams to cover at least part of the heart to be diagnosed.

3. A three-dimensional ultrasonic scan probe according to claim 2, wherein the maximum angle of diffusion at which the ultrasonic beams diffuse is set to an angle permitting the ultrasonic beams to cover the entire heart.

4. A three-dimensional ultrasonic scan probe according to claim 3, wherein the maximum angle of diffusion at which the ultrasonic beams diffuse is set to approximately 60°.

5. A three-dimensional ultrasonic scan probe according to claim 1, wherein said plurality of ultrasonic transducer elements are used in combination with an electronic scanning means that successively selects a plurality of combinations of adjoining ultrasonic transducer elements and drives ultrasonic transducer elements of each combination to transmit ultrasonic beams simultaneously.

6. A three-dimensional ultrasonic scan probe according to claim 5, wherein the maximum angle of diffusion at which the ultrasonic beams transmitted from said plurality of ultrasonic transducer elements diffuse after passing through the point at which the ultrasonic beams intersect is set to an angle, which permits the ultrasonic beams to cover the entire heart, with said three-dimensional ultrasonic scan probe placed on the chest so that the point of intersection will be located in an intercostal part.

7. A three-dimensional ultrasonic scan probe including a plurality of ultrasonic transducer elements that transmit ultrasonic beams and receive echoes so as to enable three-dimensional monitoring of a region to be measured, wherein:

an acoustic lens is placed on the top surface of said probe;

said plurality of ultrasonic transducer elements are arranged on the incidence surface of said acoustic lens so that ultrasonic beams transmitted from said ultrasonic transducer elements will intersect at a point coincident with the focus of said acoustic lens, and conically propagate over the region to be measured beyond the point of intersection.

* * * * *